US00PP31142P2

(12) United States Plant Patent
Korlipara

(10) Patent No.: US PP31,142 P2
(45) Date of Patent: Nov. 26, 2019

(54) *ECHINACEA* PLANT NAMED 'TNECHCMY'

(50) Latin Name: ***Echinacea* spp.**
Varietal Denomination: TNECHCMY

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/350,013

(22) Filed: Sep. 11, 2018

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428

CPC . A01H 5/025; A01H 5/02; A01H 5/00; A01H 6/1448; A01H 6/14
See application file for complete search history.

(56) References Cited

PUBLICATIONS

Perishable News 2018 Take A Sneak Peek At *Echinacea* Cara Mia Yellow ('TNECHCMY') PPAF, retrieved on Aug. 8, 2019, retrieved from the Internet at https://www.perishablenews.com/floral/take-a-sneak-peek-at-echinacea-cara-mia-yellow-tnechcmy-ppaf/, 3 pp. (Year: 2018).*

* cited by examiner

*Primary Examiner* — June Hwu
(74) *Attorney, Agent, or Firm* — Klarquist Sparkman, LLP

(57) ABSTRACT

A new and distinct *Echinacea* plant named 'TNECHCMY' characterized by enlarged disc florets forming an anemone-type inflorescence, yellow ray florets and yellow-orange disc florets, ray florets which are held horizontally to drooping, a short, upright habit with excellent stem count, and excellent vigor.

1 Drawing Sheet

Botanical denomination: *Echinacea* spp.
Variety designation: 'TNECHCMY'.
Trademark designation: Cara Mia$^{TM}$ Yellow.

BACKGROUND OF THE INVENTION

The present invention relates to a new and distinct cultivar of *Echinacea* and given the cultivar name 'TNECHCMY'. *Echinacea* is in the family Asteraceae. The new cultivar is part of a planned breeding program for a landscape series with compact habits and profuse, double inflorescences. The exact parents of this selection are unknown, unnamed, proprietary interspecific hybrids bred from *Echinacea paradoxa, Echinacea purpurea,* and *Echinacea tennesseensis.*

Compared to *Echinacea* 'Meteor Yellow', U.S. Plant Pat. No. 25,149, the new cultivar is shorter.

This new *Echinacea* cultivar is uniquely distinguished by:

1. enlarged disc florets forming an anemone-type inflorescence,
2. yellow ray florets and yellow-orange disc florets,
3. ray florets which are held mostly horizontally to drooping,
4. a short, upright habit with excellent stem count, and
5. excellent vigor.

This new cultivar has been reproduced by asexual propagation in Canby, Oreg., and has shown the foregoing characteristics and distinctions come true to form, and are transmitted through succeeding propagations. Propagation was conducted in tissue culture using standard micropropagation techniques by dividing terminal and lateral shoots. Each of the progeny exhibits identical characteristics to the original plant. The present invention has not been evaluated under all possible environmental conditions. The phenotype may vary with variations in environment without a change in the genotype of the plant.

DETAILED PLANT DESCRIPTION

Figure 1:
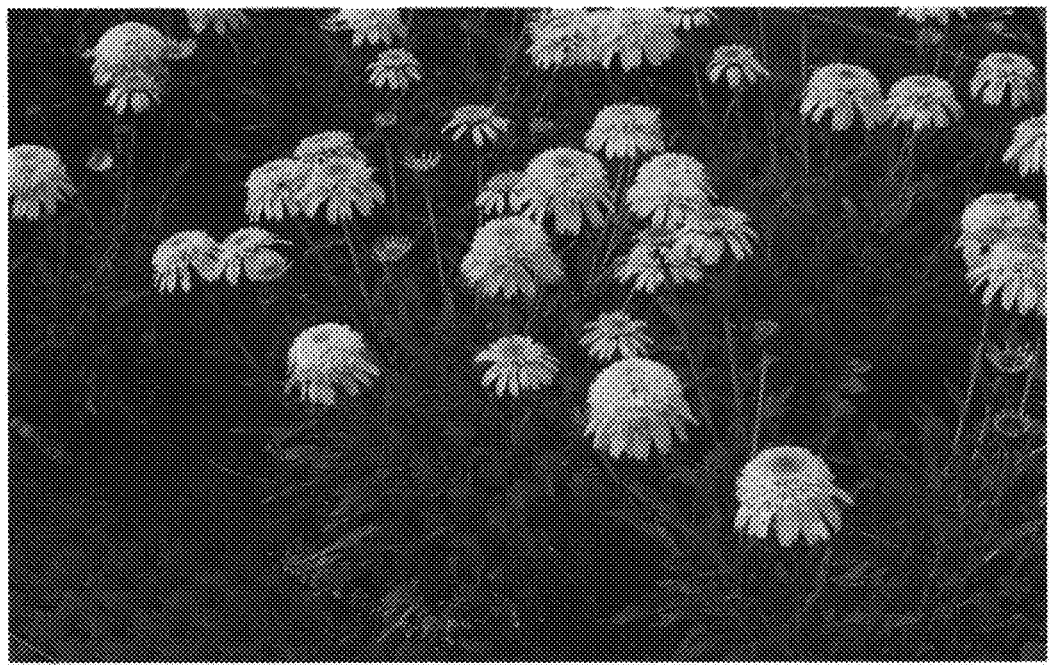
FIGS. 1 and 2 show a 17-month-old *Echinacea* 'TNECHCMY' growing in the trial field in full sun in late July in Canby, Oreg.
Figure 2:
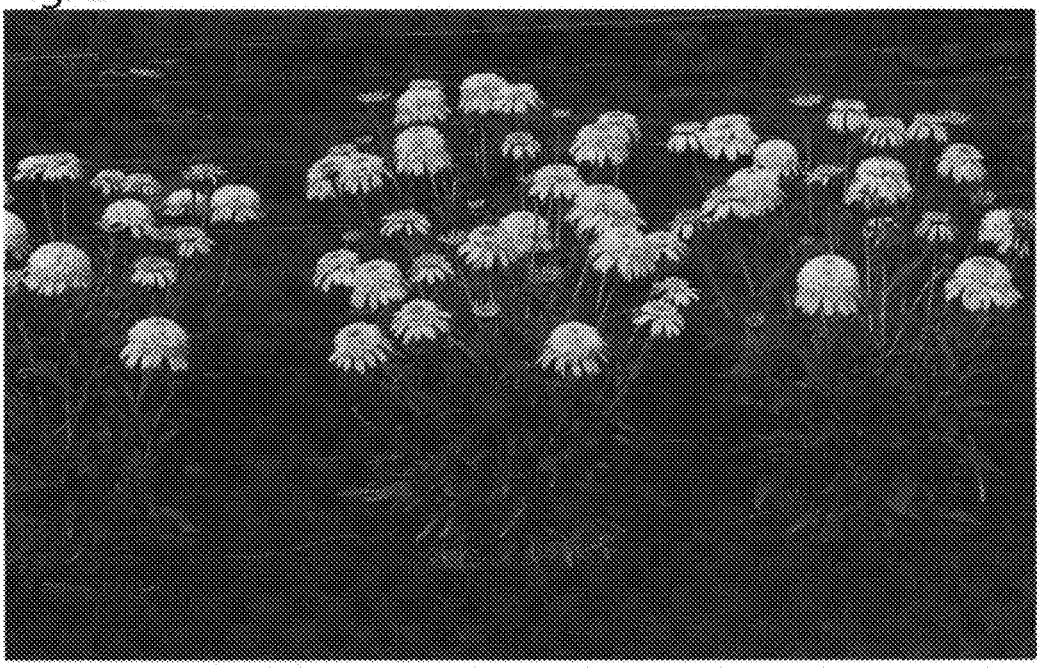

The following is a detailed description of the new *Echinacea* cultivar based on observations of 17-month-old specimens growing in the trial bed in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The *Royal Horticultural Society Colour Chart,* 5$^{th}$ edition, 2007.

Plant:

*Type.*—Herbaceous perennial.

*Hardiness.*—USDA Zones 4 to 9.

*Size.*—Grows to 43 cm wide and 40 cm tall to top of inflorescences.

*Form.*—Basal clump, with about 14 stems from the base.

*Vigor.*—Excellent.

*Roots*.—Fibrous, with many downward growing and few laterals, ivory in color, Yellow White 158D, roots develop easily from cuttings from the crown.

Stem (flowering):

*Type*.—Ascending, with 1 to 5 inflorescences per stem.

*Size*.—To 36 cm tall to a terminal inflorescence and 5 mm wide at base.

*Strength*.—Excellent.

*Internode length*.—2 cm to 4 cm.

*Surface texture*.—Strigose.

*Rugosity*.—Absent.

*Variegation*.—Absent.

*Color*.—Yellow Green 146C.

Leaf (basal):

*Type*.—Simple.

*Shape*.—Lanceolate.

*Arrangement*.—Alternate, with about 13 leaves on the main stem.

*Blade size*.—Grows to 21 cm long and 8.5 cm wide.

*Margins*.—Sparsely serrate to entire.

*Apex*.—Acuminate.

*Base*.—Attenuate.

*Surface texture*.—Strigose on both sides.

*Rugosity*.—Absent.

*Venation*.—Pinnate, Yellow Green 145C on both sides.

*Variegation*.—Absent.

*Color*.—Topside Green N137C, bottom side closest to Yellow Green 147B.

*Petiole description*.—Clasping, grows to 4 cm long and 3 mm wide, scabrous, narrow leafy edges, both sides Yellow Green 145C.

Leaf (stem):

*Type*.—Simple.

*Shape*.—Lanceolate.

*Arrangement*.—Alternate, with about 13 leaves on the main stem.

*Blade size*.—Grows to 9 cm long and 3.2 cm wide.

*Margins*.—Sparsely serrate to entire.

*Apex*.—Acuminate.

*Base*.—Attenuate.

*Surface texture*.—Strigose on both sides.

*Rugosity*.—Absent.

*Venation*.—Pinnate, Yellow Green 145C on both sides.

*Variegation*.—Absent.

*Color*.—Topside Green N137C, bottom side closest to Yellow Green 147B.

*Petiole description*.—Clasping, grows to 4 cm long and 3 mm wide, scabrous, narrow leafy edges, both sides Yellow Green 145C.

Inflorescence:

*Type*.—Composite on terminal stalked heads.

*Flowering stem*.—24 cm tall from the base of the plant to the terminal leaves below the peduncle; branched with 1 to 5 inflorescences per stem, (usually 1 at this age); diameter growing to 4 mm wide near the inflorescence; strigose; Yellow Green 146C.

*Peduncle*.—11.5 cm long from above terminal leaves to flower, 3.5 cm wide, strigose; Yellow Green 146C.

*Size*.—Grows to 9 cm wide and 7 cm deep as disc enlarges.

*Form*.—Ray florets held slightly down, reflexing more in older inflorescences, mature disc is conic.

*Immature inflorescence* (*bud*).—2.5 cm wide and 2 cm deep, ray florets held mostly upright and rolled up so only the back color shows, Yellow Orange 18B, disc color Yellow Green 144A.

*Ray florets*.—Ligulate, curvature is absent, without pistil or stamen, to 20 in number, 48 mm long and 8 mm wide, oblanceolate with the tip three-toothed (each acute), teeth cut 2 mm to 10 mm deep, florets with entire margin, base attenuate, glabrous on both sides, horizontal to drooping attitude at origin; newly fully open florets topside Yellow 13A, bottom side Yellow Orange 16D; florets lighten to Yellow 9B near base blending to Yellow 8C at top, bottom side Yellow Orange 16D.

*Disc*.—Anemone, flat becoming conic, becoming to 40 mm deep and 70 mm wide with maturity, overall color Yellow Orange 16A.

*Disc florets*.—Curvature weakly reflexed, about 480 in number, mature flowers each with 1 pistil and 4 stamen, grow to 30 mm long and 10 mm wide, each with one persistent, very stiff, linear bract (9 mm long with 3 mm Yellow Orange 16A at apex blending to 3 mm Yellow Green 144A to White 155A at base); showy 3 to 5-lobed corollas to 28 mm long and 10 mm wide, tubular on the bottom with the lobes spread out like a fan if 3-lobed (if 4 or 5-lobed the extra lobes are linear segments), glabrous on both sides; back side Yellow Orange 16D, inside Yellow Orange 16A; pistil 12 mm long, ovary 3.5 mm long, White NN155A, style 5 mm long White 155A, 2-branched stigma spreading 2 mm wide, Yellow 13A; stamen 4 mm long and thread-like, anthers 1.5 mm long and Greyed Brown N199A, filaments 2.5 mm long, White 155A, pollen none, little to no difference in color as flowers mature.

*Involucral bracts*.—In 4 leafy series, area grows to 35 mm wide and 12 mm deep, lobes lanceolate in shape, reflexed, grow to 8 mm long and 3 mm wide, Green 137A, margins strigose, tip acute, strigose on both sides.

*Receptacle*.—Grows to 15 mm wide and 17 mm deep, White NN155B.

*Bloom period*.—July through October in Canby, Oreg.

*Fragrance*.—Slight.

*Lastingness*.—Each inflorescence lasts about two weeks in Canby, Oreg.

Seeds: None seen.

*Fertility*.—None.

Disease and pests: No pests or diseases have been observed on plants grown under commercial conditions in Canby, Oreg. No resistances are known.

I claim:

1. A new and distinct *Echinacea* plant as herein illustrated and described.

* * * * *